US009445823B2

(12) United States Patent
Harris et al.

(10) Patent No.: US 9,445,823 B2
(45) Date of Patent: Sep. 20, 2016

(54) GUIDING TOOL

(75) Inventors: Nick Harris, Leeds (GB); Paul James Kistle, Wroughton (GB); Paul Smirthwaite, Bath (GB)

(73) Assignee: Biomet UK Healthcare Limited (GB)

( * ) Notice: Subject to any disclaimer, the term of this patent is extended or adjusted under 35 U.S.C. 154(b) by 298 days.

(21) Appl. No.: 13/700,933

(22) PCT Filed: Jun. 3, 2011

(86) PCT No.: PCT/GB2011/051055
§ 371 (c)(1),
(2), (4) Date: Apr. 5, 2013

(87) PCT Pub. No.: WO2011/151657
PCT Pub. Date: Dec. 8, 2011

(65) Prior Publication Data
US 2013/0190766 A1    Jul. 25, 2013

(30) Foreign Application Priority Data

Jun. 3, 2010  (GB) .................... 1009305.2

(51) Int. Cl.
*A61B 17/15*  (2006.01)
*A61F 2/42*   (2006.01)
*A61B 17/17*  (2006.01)

(52) U.S. Cl.
CPC ............. *A61B 17/15* (2013.01); *A61B 17/157* (2013.01); *A61B 17/1739* (2013.01); *A61B 2017/1775* (2013.01); *A61B 2017/1782* (2013.01); *A61F 2002/4205* (2013.01)

(58) Field of Classification Search
CPC ............... A61B 17/15; A61B 17/151–17/158; A61B 17/1764; A61B 2017/1775; A61B 2017/1782; A61B 2017/1739
USPC .......................................... 606/87, 88, 102
See application file for complete search history.

(56) References Cited

U.S. PATENT DOCUMENTS

| 356,023   | A | * | 1/1887  | Aston ............................. 108/8 |
| 819,098   | A | * | 5/1906  | Underhill ........................ 16/355 |
| 5,269,794 | A | * | 12/1993 | Rexroth ......................... 606/180 |
| 5,632,759 | A | * | 5/1997  | Rexroth ......................... 606/180 |

(Continued)

FOREIGN PATENT DOCUMENTS

| EP | 1393696 A1 | 3/2004 |
| FR | 2703584 A1 | 10/1994 |

(Continued)

OTHER PUBLICATIONS

"International Application Serial No. PCT/GB2011/051055, International Preliminary Report on Patentability mailed Dec. 13, 2012", 8 pgs.

(Continued)

*Primary Examiner* — Matthew Lawson
*Assistant Examiner* — Amy Sipp
(74) *Attorney, Agent, or Firm* — Schwegman Lundberg & Woessner, P.A.

(57) ABSTRACT

A guiding tool (2) is disclosed comprising a tool body (4) that defines a reference plane of the tool (2); an alignment member (10) that carries a guide surface (74); and an adjustment means acting between the tool body (4) and the alignment member (10) to direct rotational adjustment of the alignment member (10) with respect to the tool body (4).

21 Claims, 15 Drawing Sheets

(56) References Cited

U.S. PATENT DOCUMENTS

| | | | |
|---|---|---|---|
| 5,681,316 A | 10/1997 | DeOrio et al. | |
| 2005/0049603 A1* | 3/2005 | Calton et al. | 606/87 |
| 2005/0154394 A1 | 7/2005 | Michalowicz | |
| 2006/0149276 A1* | 7/2006 | Grimm | 606/88 |
| 2006/0247646 A1* | 11/2006 | Bihary et al. | 606/87 |

FOREIGN PATENT DOCUMENTS

| | | |
|---|---|---|
| FR | 2770765 A1 | 5/1999 |
| WO | WO-2011151657 A1 | 12/2011 |

OTHER PUBLICATIONS

"International Application Serial No. PCT/GB2011/051055, International Search Report mailed Aug. 16, 2011", 4 pgs.

"International Application Serial No. PCT/GB2011/051055, Written Opinion mailed Aug. 16, 2011", 6 pgs.

United kingdom Application Serial No. 1009305.2, Examination Report mailed Mar. 30, 2016, 3 pgs.

* cited by examiner

GUIDING TOOL

CROSS-REFERENCE TO RELATED APPLICATIONS

This application is a U. S. national stage of International Application No. PCT/GB2011/051055, filed on Jun. 3, 2011 and published in English as WO2011/151657 on Dec. 8, 2011. This application claims the benefit of Great Britain Application No. 1009305.2, filed on Jun. 3, 2010. The disclosures of the above applications are incorporated herein by reference.

The present invention relates to a guiding tool and particularly but not exclusively to a guiding tool for guiding resection of a bone during a joint replacement or resurfacing procedure. The guiding tool of the present invention is particularly suited for use in procedures concerned with the ankle, elbow and wrist.

BACKGROUND

It is known to replace diseased or damaged articulating surfaces of a joint with prosthetic components in total or partial joint replacement procedures. During such procedures, damaged bone tissue is cut away, leaving clean resected bone surfaces for attachment of prosthetic components. Correct positioning of the resected surfaces is vital to ensuring correct balancing of soft tissues and transfer of forces through the reconstructed joint. Guide tools are conventionally employed to direct the correct positioning of bone cuts with reference to patient anatomy. For example, in a total ankle replacement procedure, it is considered desirable to resect the distal tibia along a plane that is perpendicular to the longitudinal axis of the tibia. Guide tools are known that align with the long axis of the tibia and present a guide surface that is perpendicular to this long axis, thus directing perpendicular resection of the distal tibia. There are circumstances however when alignment with reference to conventional physical features can be difficult and/or disadvantageous. For example, for patients with a bowed or otherwise abnormal tibia, resection of the distal tibia with reference to the tibial long axis can be difficult to achieve, and may result in less than optimal transmission of forces through the joint.

SUMMARY OF INVENTION

According to the present invention, there is provided a guiding tool comprising a tool body that defines a reference plane of the tool; an alignment member that carries a guide surface; and an adjustment means acting between the tool body and the alignment member to direct rotational adjustment of the alignment member with respect to the tool body.

The adjustment means may be configured to direct rotational adjustment of the alignment member in the reference plane of the tool.

The guiding tool may further comprise a referencing rod that is connectable to the alignment member and operable for alignment with a reference axis.

The referencing rod may be connectable to the alignment member in a predetermined angular relation to the guide surface.

The guide surface may be planar and the referencing rod may be connectable to the alignment member such that a longitudinal axis of the referencing rod is substantially normal to the plane of the guide surface.

The referencing rod may be connectable via a threaded connection.

The adjustment means may comprise an adjustment pin that may be received through an arcuate slot on the alignment member to engage a recess on the tool body.

The pin and recess may carry cooperating external and internal threads.

The adjustment means may further comprise a guide plate extending from an end of the tool body and received within a guide slot formed in the alignment member.

The guide plate and slot may extend parallel to the reference plane or may extend in the reference plane of the tool.

The guiding tool may further comprise an indicator, operable to indicate a default position of rotational adjustment in which the guide surface of the alignment member is in a predetermined angular relation to the reference plane of the tool. The predetermined angular relation may for example be 90 degrees.

The indicator may comprise a protrusion formed on one of the tool body and the alignment member and a corresponding recess formed on the other of the tool body and the alignment member. The protrusion may comprise a spring mounted ball and the recess may comprise a groove extending along an axis that defines the position at which the alignment member is in the predetermined angular relation with the reference plane of tool.

The tool body may comprise a tool stem and a translation member which is translatable with respect to the tool stem along a translation axis.

The guiding tool may further comprise a threaded driving connection between the tool stem and the translation member. The driving connection may comprise a threaded shaft formed on one of the translation member and tool stem and a cooperating captive nut with gripping surface, rotatably held within the other of the translation member and the tool stem.

The adjustment means may act between the translation member and the alignment member. Reference scales may be marked on at least one of the tool stem, translation member and alignment member, operable to indicate magnitudes of translational and rotational adjustment.

The tool body may comprise at least two telescoping sections, each of which may comprise a part of the tool stem.

The tool body may further comprise at least two fixation members disposed at opposed ends of the tool stem and operable to allow fixation of the tool to a patent's anatomy.

A first fixation member may comprise opposed jaws. A second fixation member may comprise at least two opposed fixation blocks, each fixation block comprising a plurality of guide holes extending there through and operable to receive a plurality of fixation elements, which may for example comprise bone pins.

The guiding tool may comprise a guiding tool for an ankle. The guide surface may be a distal tibial cutting guide surface.

In use, the reference plane of the tool may be parallel to a coronal plane of a patient. The referencing rod may be operable for alignment with a fibula of a patient According to another aspect of the present invention, there is provided a guiding tool for guiding resection of a distal tibia as part of a total ankle replacement procedure, the guiding tool comprising a tool body having fixation members for fixation relative to a tibia, a cutting guide surface that is rotatable relative to the tool body and a referencing member that is connected in a predetermined angular relation to the cutting guide surface and is operable for alignment with a fibula.

The cutting guide surface may be rotatable in a plane that is perpendicular to a plane of the cutting surface.

In use, the cutting guide surface may be rotatable in a coronal plane of a patient.

According to another aspect of the present invention, there is provided guiding tool for guiding resection of a tibia, the guiding tool comprising a moveable cutting guide surface and a referencing member connected in a predetermined angular relation to the cutting guide surface, the referencing member being moveable for alignment with a fibula, such that the cutting guide surface is placed in the predetermined angular relation with respect to the fibula.

According to another aspect of the present invention, there is provided a method of resecting a tibia as part of a total ankle replacement procedure comprising: placing a guide surface adjacent to the tibia of a patient, orienting the guide surface to be in a fixed angular relation to a fibula of the patient, and resecting the first tibia along the oriented guide surface.

BRIEF DESCRIPTION OF THE DRAWINGS

For a better understanding of the present invention, and to show more clearly how it may be carried into effect, reference will now be made, by way of example, to the following drawings, in which:—

DETAILED DESCRIPTION OF EMBODIMENTS

Figure 1:
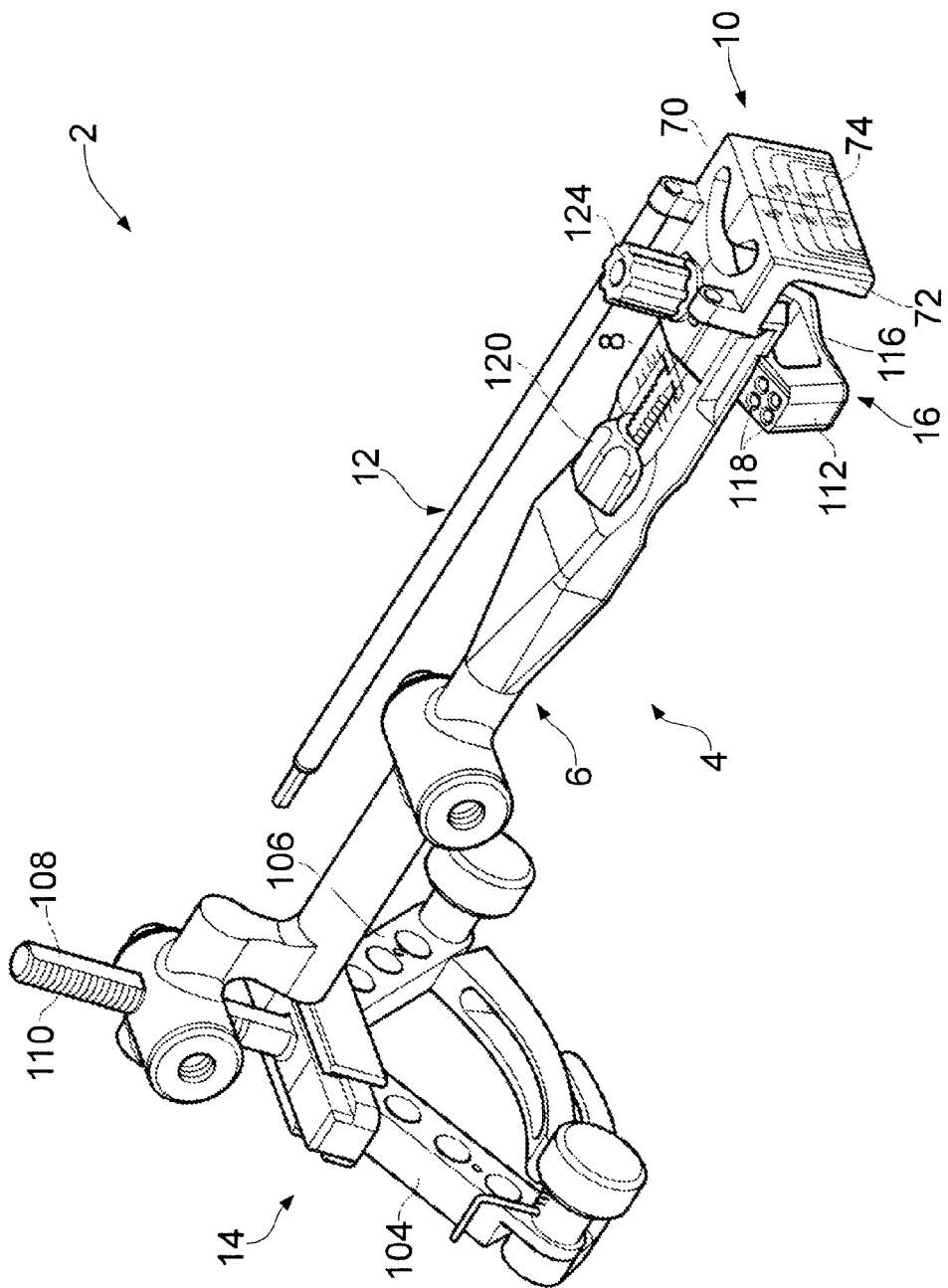
FIG. 1 is a perspective view of a guiding tool.

With reference to FIGS. 1 to 10, a guiding tool 2 comprises a tool body 4, having a stem 6 and a translation member 8, an alignment member 10 and a referencing rod 12.

First and second fixation members 14, 16 extend from opposed ends of the tool body 4.

Figure 3:
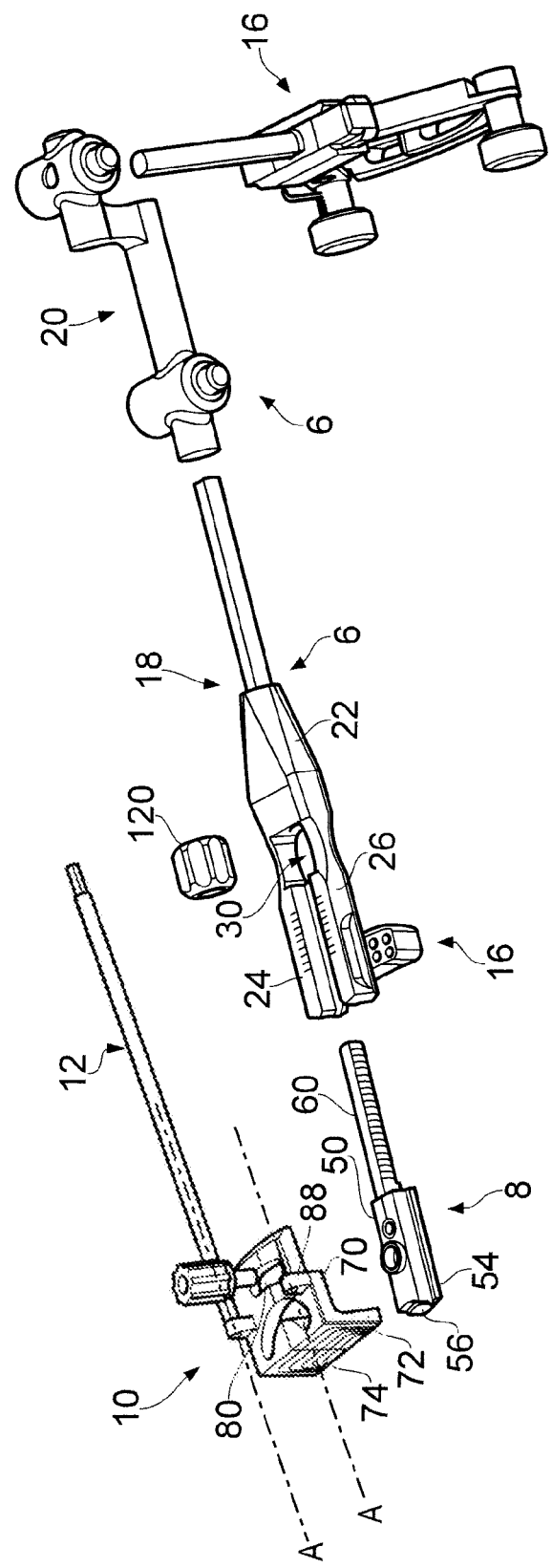
FIG. 3 is an exploded view of the component parts of a guiding tool.
Figure 4:
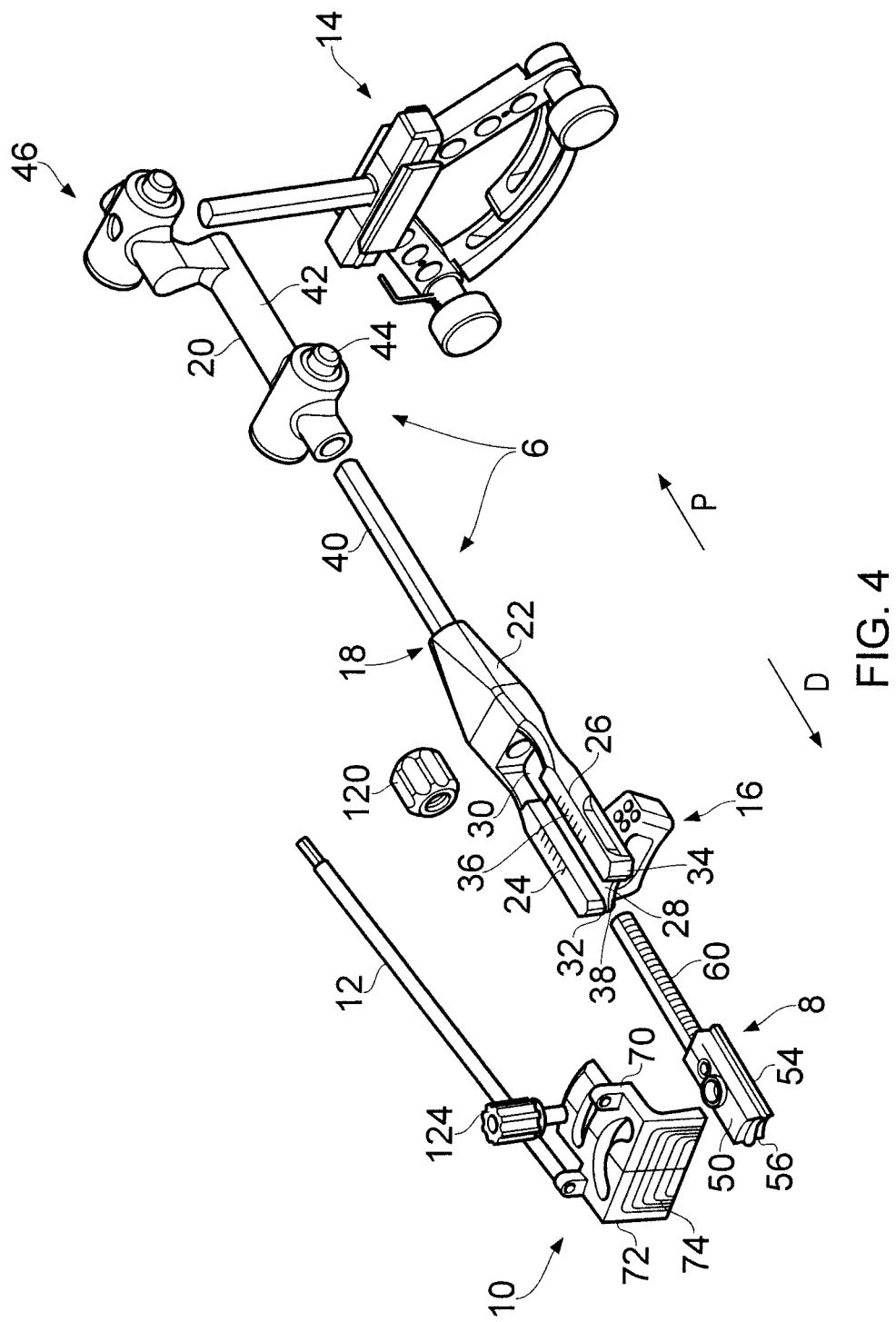
FIG. 4 is an alternate exploded view of the component parts of a guiding tool.

With particular reference to FIGS. 3 and 4, the stem 6 of the tool body 4 comprises first and second telescoping sections 18, 20. The first telescoping section 18 comprises a main body 22 from which first and second arms 24, 26 extend in a first direction D. The first and second arms 24, 26 are marked with a reference scale and define a longitudinal opening 28 there between. At a base of the longitudinal opening 28, adjacent the main body 22, the first and second arms 24, 26 define a larger diameter recess 30. Parallel longitudinal grooves 32, 34 extend along facing sides of the arms 24, 26 to define a receiving channel. A supporting plate 36 spans the longitudinal opening 28 between the first and second arms 24, 26 from a region adjacent free ends of the arms 24, 26 to a region immediately adjacent the larger diameter recess 30. A free end 38 of the supporting plate 36, adjacent the free ends of the first and second arms 24, 26, is curved in a concave manner. The second fixation member 16 is fixedly joined to the supporting plate 36 and first and second arms 24, 26, proximate the free ends of the supporting plate 36 and arms 24, 26. Further detail of the first fixation member 16 is explained below. A telescoping shaft 40 extends from the main body 22 of the first telescoping section 18 in a second direction P, opposite to the first direction D. The telescoping shaft 40 is of a rectangular or other polygonal cross section and is received within an appropriately shaped opening on the second telescoping member 20. The second telescoping member 20 comprises hollow shaft 42, dimensioned to slidably receive the telescoping shaft 40 of the first telescoping section 18. A locking pin 44 extends across the hollow shaft 42 to lock the telescoping shaft 40 of the first telescoping section 18 into a desired position within the hollow shaft 42 of the second telescoping section 20 and thus lock the first and second telescoping sections 18, 20 together. A connection feature 46 extends from the hollow shaft 42 of the second telescoping section 20 and is dimensioned to receive and connect to the first fixation member 14 in a manner that is described in further detail below.

Figure 5:
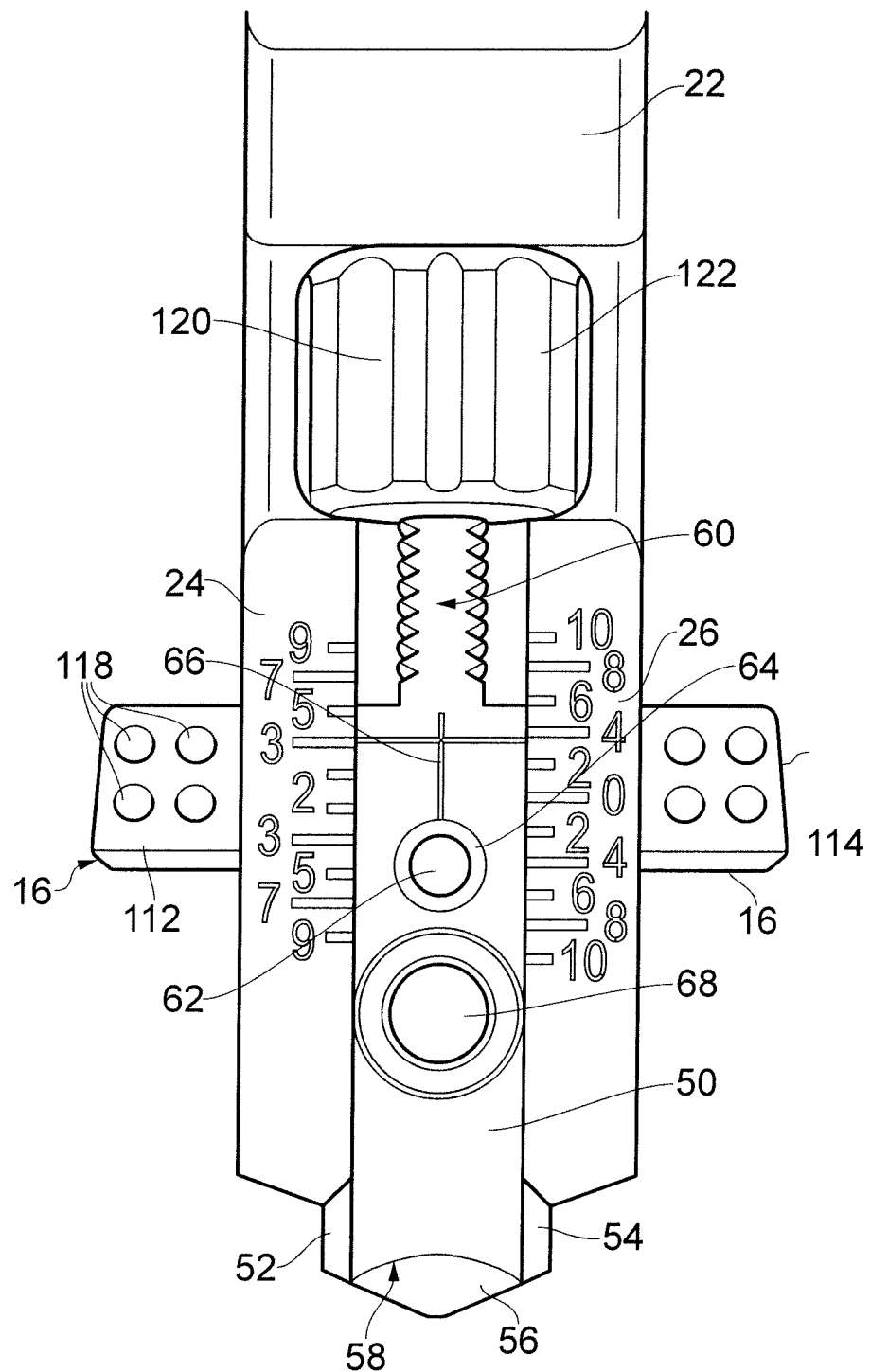
FIG. 5 is a partial frontal view of a translation member assembled into a stem of a guiding tool.
Figure 6:
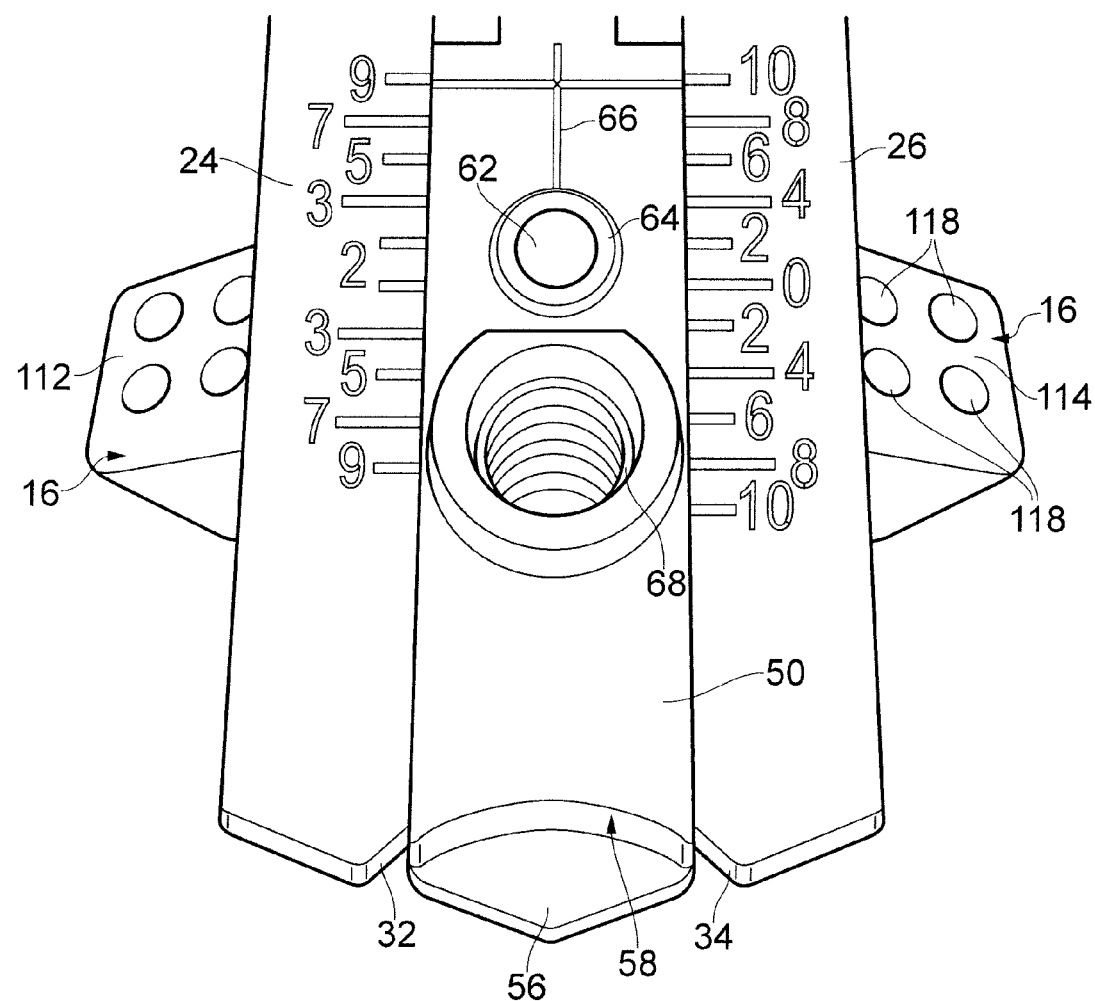
FIG. 6 another partial frontal view of the components of FIG. 5.

With reference also to FIGS. 5 and 6, the translation member 8 of the tool body 4 comprises a substantially rectangular translation plate 50 having opposed guide rails 52, 54 extending from each longitudinal side. The plane of the translation plate 50 defines a reference plane of the tool 2. A substantially triangular guide plate 56 extends from an otherwise concave curved free end 58 of the translation plate 50. At an opposite end of the translation plane 50 to the guide plate 56, a threaded shaft extends in the second direction P. A planar face of the translation plate 50 comprises a spring mounted ball bearing 62, which is held captive in the translation plate by a circular rim 64 of the translation plate 50, and may be depressed into the translation plate 50 by compressing the mounting spring (not shown). The ball bearing 62 is mounted in the translation plate 50 such that its centre is positioned precisely along a central longitudinal axis of the translation plate 50. The position of this central axis is marked by a shallow axial groove 66 that extends away from the ball bearing 62 in the second direction P. The planar face of the translation plate 50 also comprises a threaded bore 68, a central axis of which is located on the central longitudinal axis of the translation plate 50.

Figure 7:
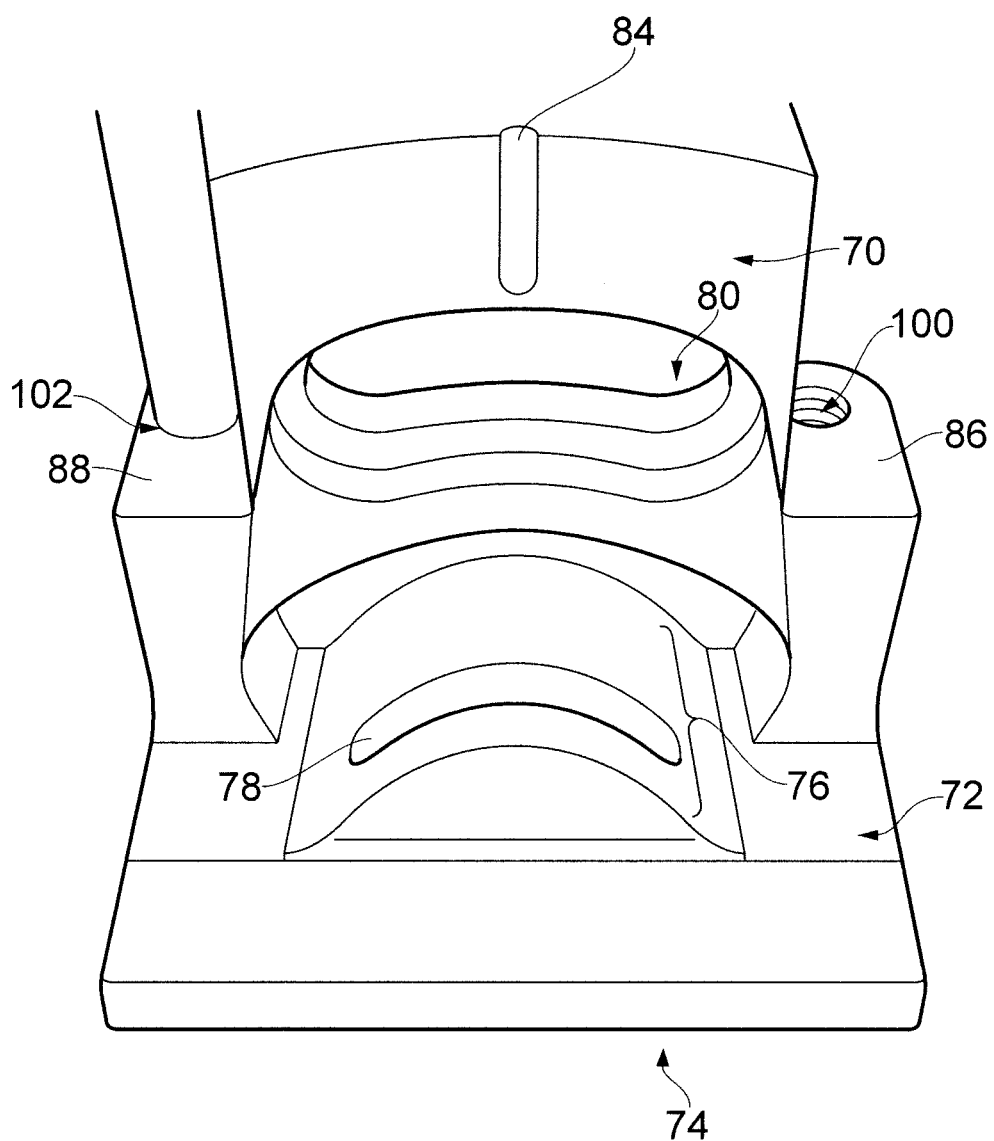
FIG. 7 is a perspective view of an alignment member of a guiding tool.
Figure 8:
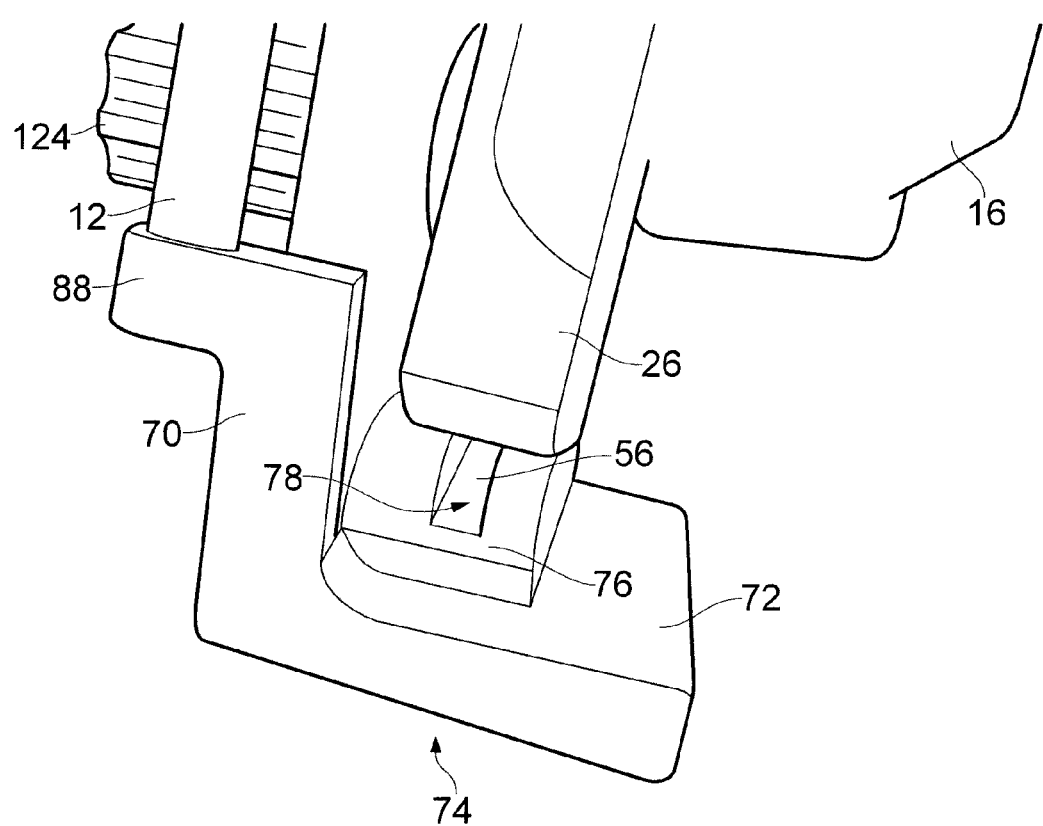
FIG. 8 is a partial side view of an alignment member assembled with a translation member and stem of a guiding tool.

Referring also to FIGS. 7 and 8, the alignment member 10 comprises an alignment plate 70 and a guide surface plate 72, the two plates being integrally formed in a substantially L shaped arrangement. The guide surface plate 72 comprises a cutting guide surface 74 on a distal surface of the guide surface plate. A guide protrusion 76 extends from an opposed surface of the guide surface plate. The guide protrusion 76 is a curved part cylindrical protrusion having a guide slot 78 extending there through. The guide slot 78 extends substantially parallel to the plane of the alignment plate 70. The alignment plate 70 comprises an arcuate guide slot 80 extending across the alignment plate 70 substantially above the guide protrusion 76. An outer face 82 of the alignment plate 70 carries a reference scale. An inner face of the alignment plate 70 comprises an indicator groove 84 that extends axially from the arcuate guide slot 80. The indicator groove 84 is dimensioned to receive and engage a protruding portion of the ball bearing 62 of the translation plate 50. Mounting protrusions 86, 88 extend from opposed sides of the alignment plate 70, each mounting protrusion comprising a threaded blind bore 100, 102, a longitudinal axis A of which is in a predetermined angular relation to the plane of the cutting guide surface 74. In a preferred embodiment, the predetermined angular alignment is 90 degrees, such that the longitudinal axes of the threaded bores 100, 102 are normal to the plane of the cutting guide surface 74. However, other angular relations between the axes of the bores 100, 102 and the plane of the cutting guide surface 74 can be contemplated. Referencing rod 12 comprises a plane rod having a threaded end, dimensioned to be received in either of the threaded blind bores 100, 102, such that the longitudinal axis of the referencing rod 12 is coincident with the longitudinal axis of the corresponding bore 100, 102.

Figure 2:
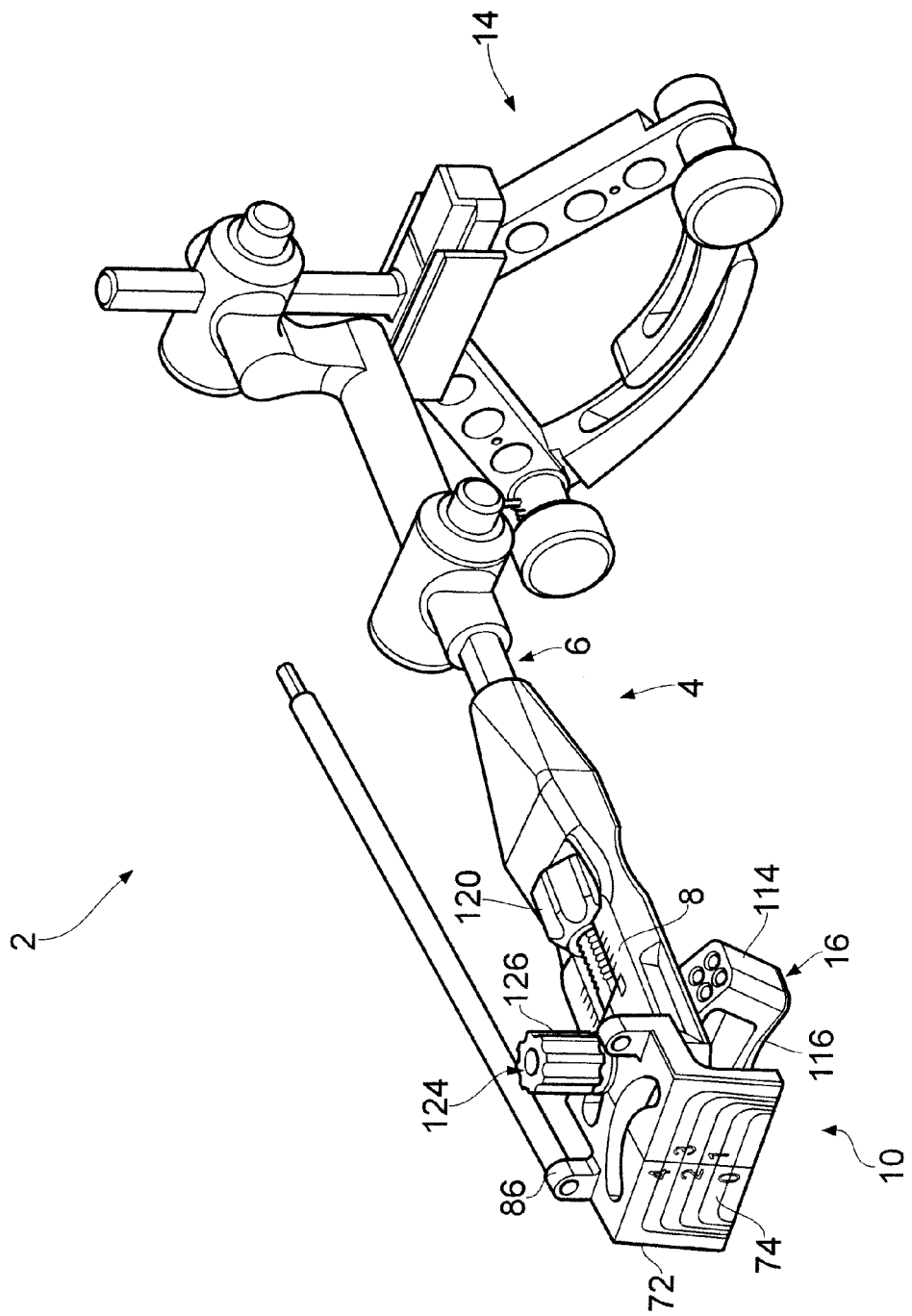
FIG. 2 is an alternate perspective view of the guiding tool of FIG. 1.

Referring particularly to FIGS. 1 and 2, the first fixation member comprises a pair of opposed articulating jaws 104, 106 mounted on an extending shaft 108 that carries a rack 110. The connection feature 46 of the second telescoping section 20 of the tool body carries an appropriate engaging tool such as a pawl to engage the rack 110 of the shaft 108. The second fixation member 16 comprises a pair of opposed mounting blocks 112, 114 joined by connecting arms 116. Each mounting block 112, 114 carries a plurality of guide holes 118, operable to receive fixation elements such as bone screws or pins. Preferably, at least four guide holes 118 extend through each mounting block 112, 114. The second fixation member 16 is fixedly attached to the stem 6 of the tool body 4 such that each mounting block 112, 114 protrudes from a distant side of a respective first or second arm 24, 26.

The guiding tool 2 is assembled in the following manner. The first and second telescoping sections 18, 20 are connected by inserting the telescoping shaft 40 of the first telescoping member 18 into the hollow shaft 42 of the second telescoping member 20 and employing the locking pin 44 to lock the first and second telescoping sections 18, 20 together. The first fixation member is then connected to the second telescoping section 20 via the shaft 108 and connection feature 46. A translation nut 120 is placed in the larger diameter recess 30 at the base of the longitudinal opening 28 defined between the first and second arms 24, 26 of the tool stem 6. The translation member 8 is then assembled into the tool stem 6 by sliding the translation plate into the longitudinal opening defined between the first and second arms 24, 26. The guide rails 52, 54 of the translation member 8 are received in the longitudinal grooves 32, 34 of the first and second arms 24, 26. As the translation member 8 is inserted into the longitudinal opening 28, the threaded shaft 60 of the translation member approached and is received within the translation nut 120. The translation nut 120 is held captive within the larger diameter recess and thus is rotated via a gripping surface 122 to allow and direct further sliding of the translation member 8 into the longitudinal opening 28. The alignment member 10 is then assembled with the tool stem 6 by inserting the protruding guide plate 56 of the translation member 8 into the guide slot 78 of the guide protrusion 76 on the alignment member 10. In this manner, a planar inner surface of the alignment plate 70, comprising the indicator groove 84, is brought into contact with the planar surface of the translation plate 50, such that the alignment plate 70 rests in the reference plane of the tool 2. With the guide plate 56 fully inserted into the guide slot 78, the arcuate guide slot 80 on the alignment plate 70 of the alignment member is disposed substantially over the threaded bore 68 of the translation member. A default orientation of the alignment member 10 is established by adjusting the alignment of the alignment member 10 until the spring mounted ball bearing 62 is received within the indicator groove 84 of the alignment plate 70 of the alignment member 10. The alignment member 10 is then held in position by a threaded angular adjustment fixation pin 124 that extends through the arcuate guide slot and engages the threaded bore 68 of the translation member 8. A protruding head 126 of the angular adjustment fixation pin 124 presents an annular shoulder to engage against the surface of the alignment plate of the alignment member 10 and thus lock the position of the alignment member 10 with respect to the translation member 8. The referencing rod 12 is then screwed into one of the threaded blind bores 100, 102 on the mounting protrusions 86, 88.

Figure 9:
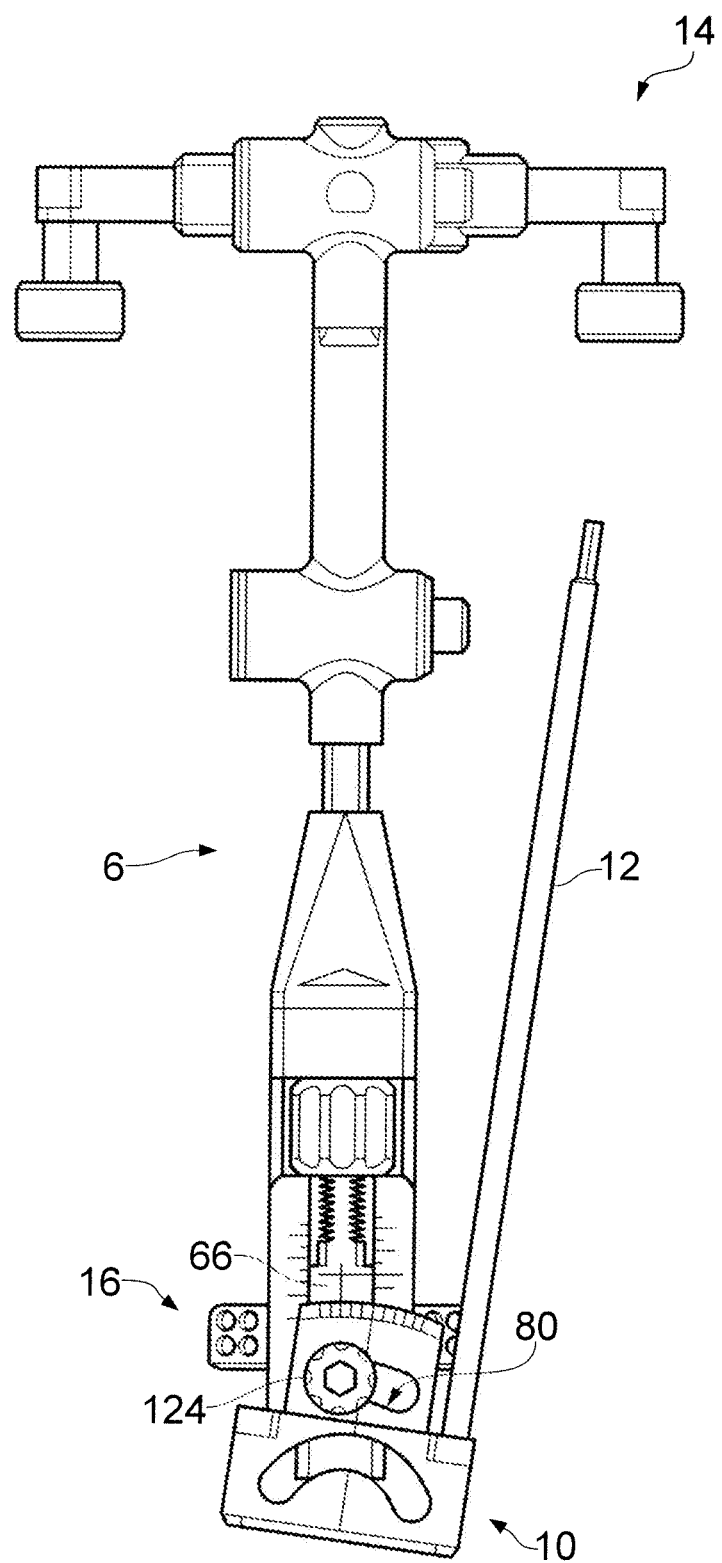
FIG. 9 is a front view of a guiding tool showing rotational adjustment.
Figure 10:
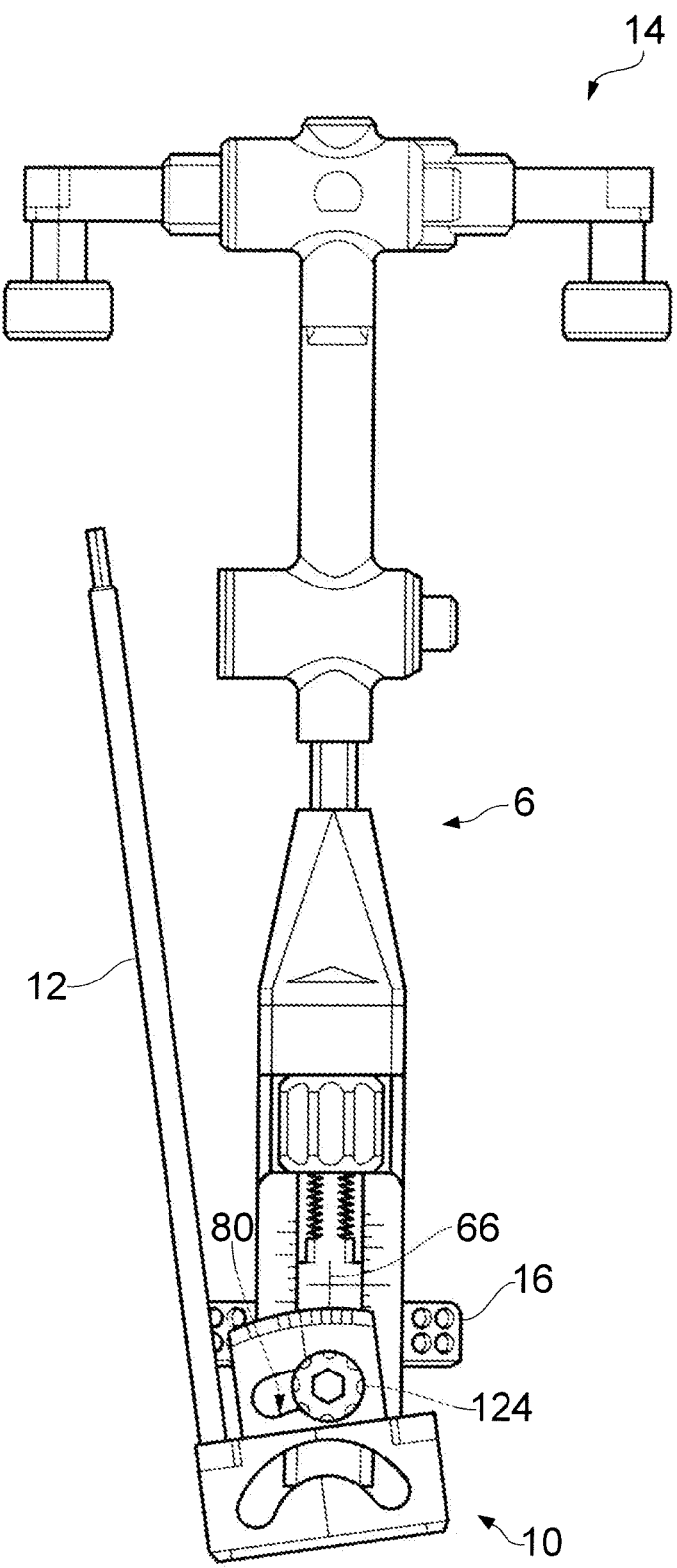
FIG. 10 is another front view of a guiding tool showing alternative rotational adjustment.

With particular reference to FIGS. 9 and 10, adjustment of the alignment member 10 is achieved as follows. First the angular adjustment fixation pin 124 is loosened by unscrewing slightly to remove the frictional lock between the alignment member 10 and the translation member 8. The alignment member 10 may then be rotated within a plane of rotation that is coincident with the reference plane of the tool and is defined by the contacting surfaces of the translation plate 50 and the alignment plate 70. Rotation in this plane is supported by the parallel action of the guide plate 56 turning in the guide slot 78. It will be appreciated that the triangular nature of the protruding guide plate 56, together with the cooperating curved surfaces of the translation plate (surface 58) and guide protrusion 76 facilitate and direct smooth rotation of the alignment member 10. The scale on the alignment plate 70 of the alignment member 10 can be used in conjunction with the axial groove 66 on the translation member 8 to provide an indication of the degree of rotation of the alignment member 10. Once the desired degree of rotational adjustment has been achieved, the angular adjustment fixation pin 124 is rotated to screw the angular adjustment fixation pin 124 back into the threaded bore 68 of the translation member 8 and lock, via the head 126, the alignment member 10 and the translation member 8 together. It will thus be appreciated that the angular adjustment fixation pin 124, the arcuate guide slot 80, the protruding guide plate 56 and the guide slot 78 together function as an adjustment means, facilitating, directing and constraining rotational adjustment of the alignment member 10 with respect to the translation member 8 in a rotational plane.

Use of the guiding tool 2, is now described with reference to a total ankle replacement operation as illustrated in FIGS. 11 to 15. It will be appreciated however, that this tool may also be employed in for example procedures involving the wrist and elbow.

Figure 11:
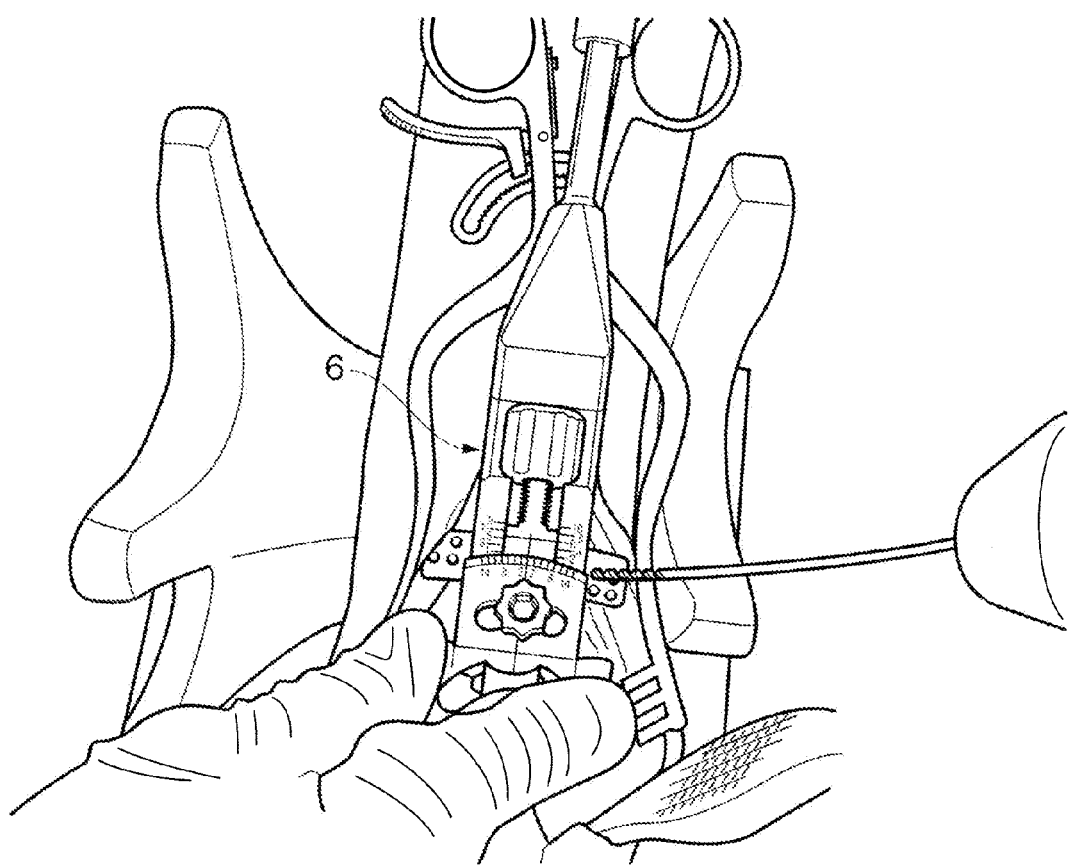
FIG. 11 is a representative image of a guiding tool in use.

In a total ankle replacement procedure, an incision is first made and soft tissues retracted to give access to the joint. The assembled guiding tool 2 is then placed against the lower limb of the patient and fixed in position. The translation member 8 is translated away from the rest of the tool 2 to its fullest extent by rotating the translating nut 120. The opposing jaws 104, 106 of the first fixation member 14 clamp around an upper region of the lower limb of the patient, below the knee joint. The telescoping sections 18, 20 of the stem 6 of the tool 2 are extended or retracted in order to achieve the correct length of stem for the individual patent concerned and are locked in position using the locking pin 44. With the opposing jaws 104, 106 of the first fixation member 14 in place, the stem of the guiding tool 2 follows the major axis of the tibia and the cutting guide surface 74 is positioned to allow removal of the protruding lip of the distal tibia. The distal end of the tool 2 is then fixed in position on the revealed tibial bone by inserting fixation pins 130 through the guide holes 118 on the mounting members 112 114 of the second fixation member 16. The fixation pins are inserted into bone holes drilled through the guide holes 118 using a surgical drill, as shown in FIG. 11. It will be appreciated that the plurality of guide holes in the mounting blocks 112, 114 provide a range of options for the precise location of the fixation pins 130. Thus, if one or more of the guide holes are located above voids in the bone, such as may be present in a diseased or damaged ankle, another guide hole 118 may be used that is located above healthy bone that will provide appropriate fixation.

Figure 12:
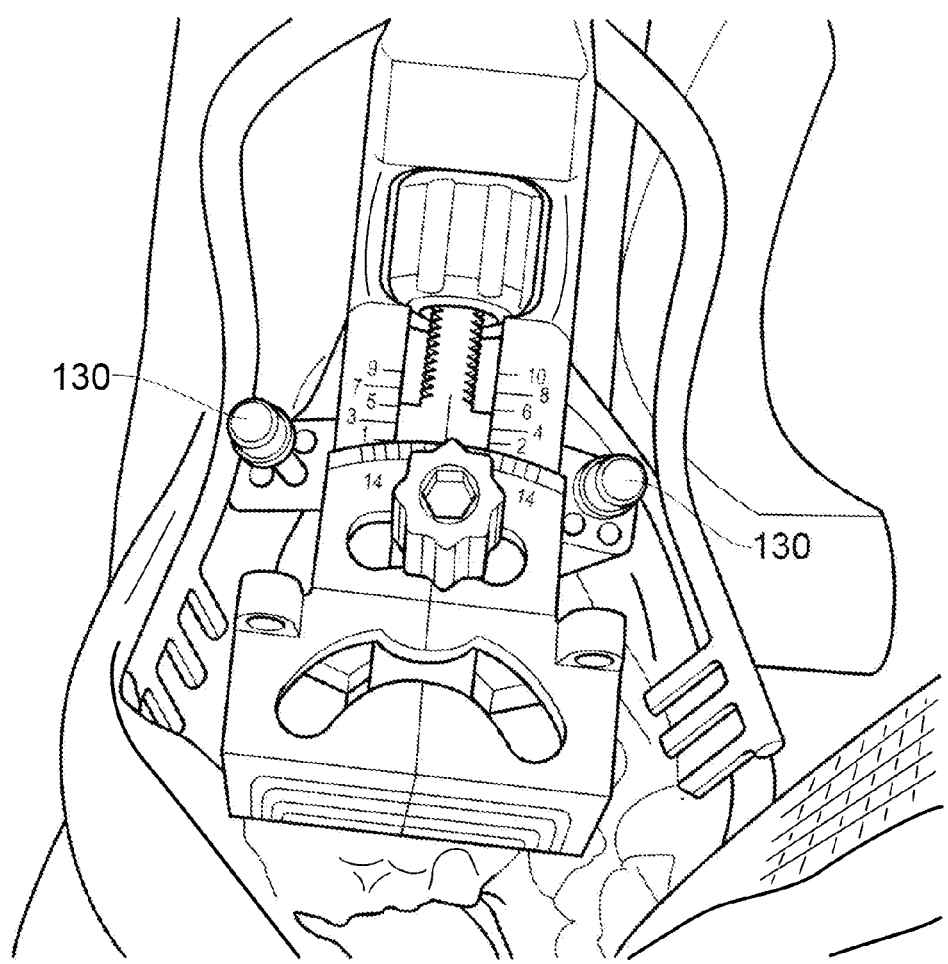
FIG. 12 is a representative view of a guiding tool when fixed in place on a patient.
Figure 13:
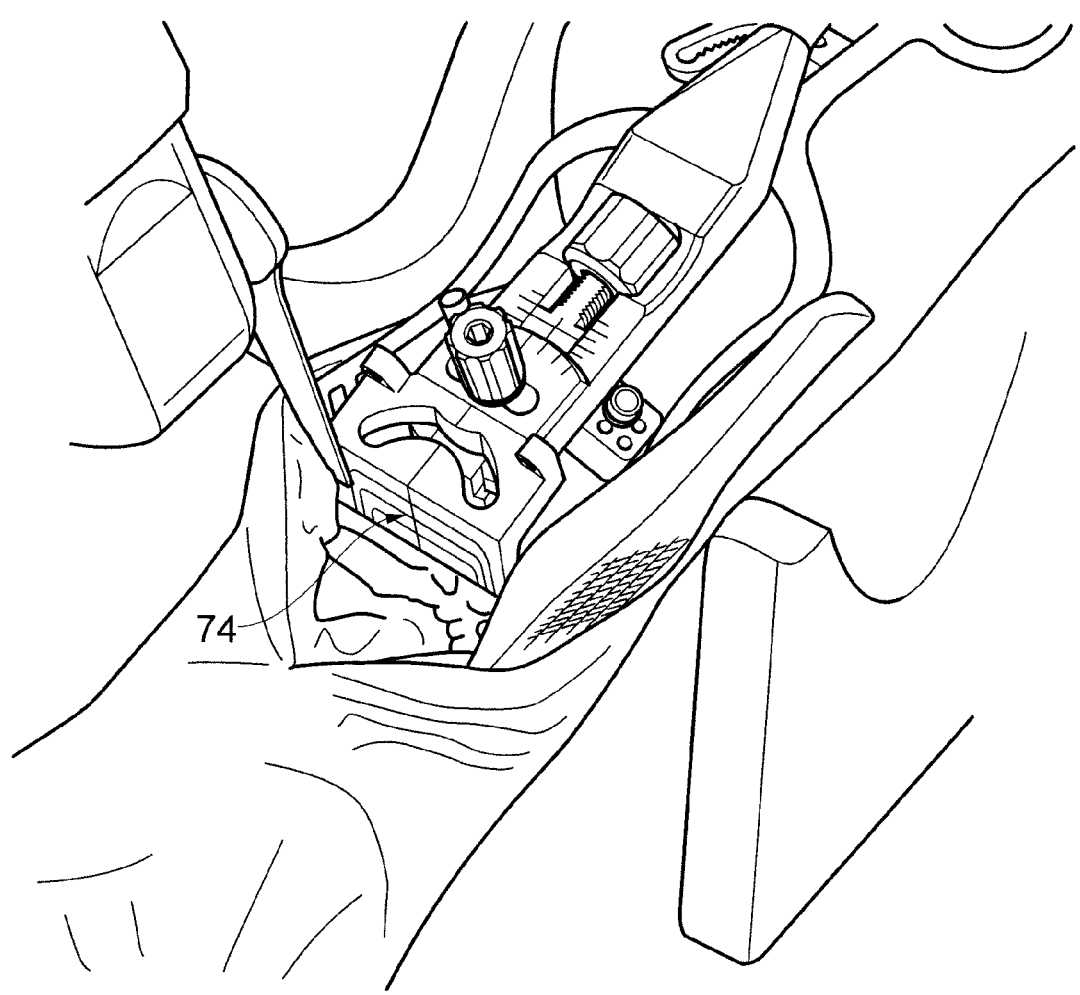
FIG. 13 is a representative view of a guiding tool guiding resection of a tibial lip.

With the guiding tool 2 fixed in place as shown in FIG. 12, a saw blade is placed against the cutting guide surface 74 and used to remove the lip of the distal tibia, as shown in FIG. 13, thus affording improved access to the joint cavity.

Figure 14:
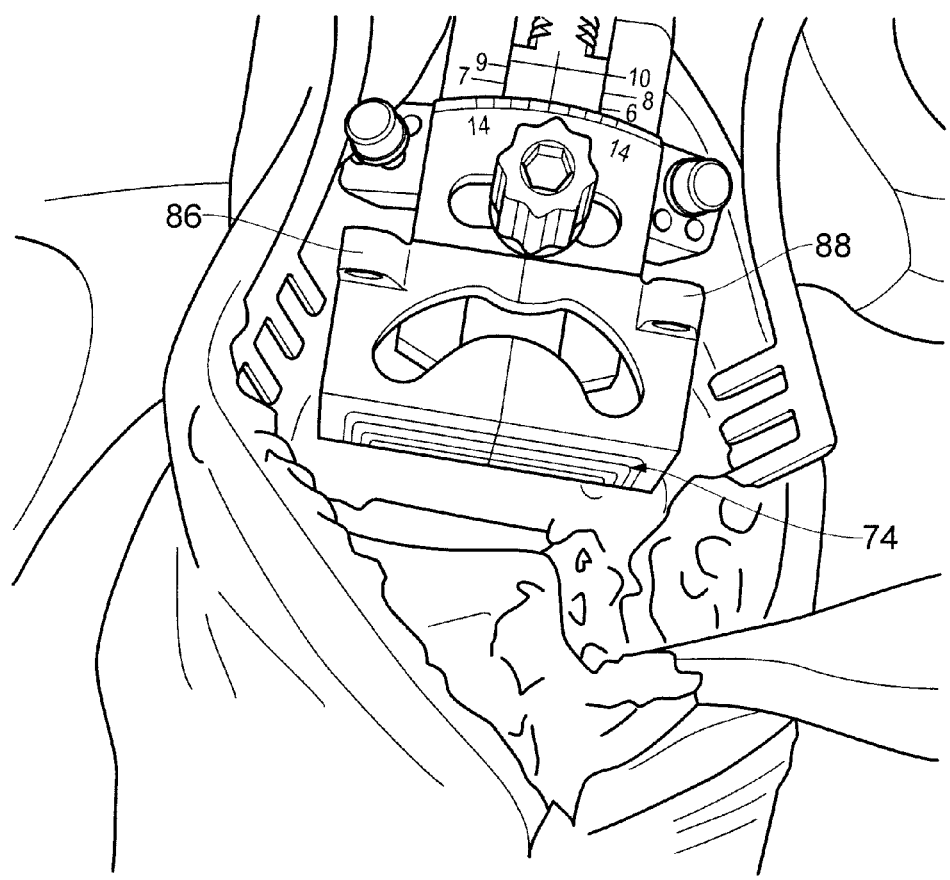
FIG. 14 is a representative view of a guiding tool illustrating translation of a translation member.
Figure 15:
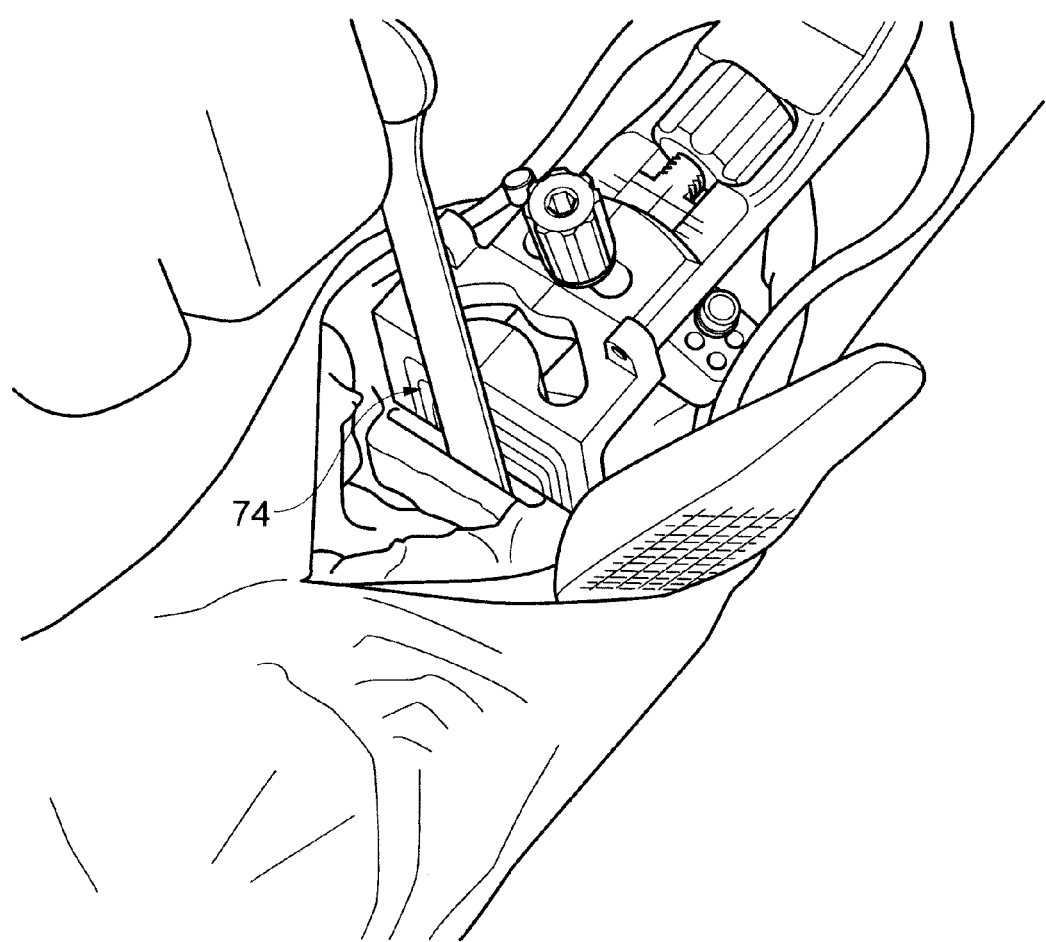
FIG. 15 is a representative view of a guiding tool guiding resection of a distal tibia.

The translation member 8 and mounted alignment member 10 are then translated back towards the tool 2 by rotating the translation nut 120 until the cutting guide surface is at the correct level to perform the main distal tibial resection, as illustrated in FIG. 14. At this point, the referencing rod 12 is attached to the appropriate mounting protrusion 86, 88 depending upon whether it is a left or right ankle that is being reconstructed. The angular adjustment fixation pin 124 is released slightly, to allow angular adjustment of the alignment member 10 in the manner described above. With the tool 2 fixed in position on a patent, the plane of rotation of the alignment member is coincident with a frontal or coronal plane of the patent. A "C arm" unit is put in place about the patient and with this in position, the referencing rod 12 is moved until it is placed in alignment with the long axis of the fibula. The threaded connection between the referencing rod 12 and the alignment member 10 ensures that the referencing rod can only move with the alignment member. The referencing rod is thus moved in the frontal plane of the patent, with the alignment member rotating in that plane, facilitated by the adjustment means. Once the desired orientation of the referencing rod 12 with the fibula has been achieved, the angular adjustment fixation pin 124 is tightened to fix the rotational position of the alignment member 10 with respect to the translation member 8. The plane of the cutting guide surface 74 is thus placed in the predetermined angular relation of 90 degrees with the log axis of the fibula. A saw blade is then placed against the cutting guide surface 74 and the distal tibial resection is made as illustrated in FIG. 15. Any remaining osteophytes and bony growths attached to the soft tissues can be individually removed as necessary. With the tibial resection complete, the guiding tool 2 is removed from the wound and the total ankle replacement procedure can proceed in any appropriate manner.

It will be understood that the guiding tool 2 of the present invention facilitates a new method of performing the distal tibial resection in a total ankle replacement procedure. The inventors of the guiding tool 2 have discovered that force transmission through the reconstructed ankle is improved if the distal tibia is resected perpendicular to the long axis of the fibula, instead of perpendicular to the long axis of the tibia, as is conventional. Not only does a resection in this manner provide improved force transmission, but it also allows for improved certainty and repeatability, as the problems associated with bowed or otherwise deformed tibias are avoided. The guiding tool of the present invention may also be employed in other procedures where it is desired to resect a first bone at a predetermined angle to an axis of a second bone. The referencing rod 12 of the guiding tool may be aligned with any desired referencing feature in order to place the cutting guide surface in a perpendicular alignment to the reference feature. It will be further appreciated that the angular relation between the referencing rod and the cutting guide surface need not be perpendicular. Any desired predetermined angular relation can be contemplated. Controlled adjustment of the angular relation between the referencing rod 12 and the cutting guide surface 74 can also be contemplated, to allow greater freedom to a surgeon in selecting the desired orientation and alignment of bone cuts.

The invention claimed is:

1. A surgical guiding tool comprising:
a tool body that defines a reference plane of the tool;
an alignment member that carries a guide surface; and
an adjustment mechanism acting between the tool body and the alignment member configured to direct rotational adjustment of the alignment member with respect to the tool body,
wherein the adjustment mechanism includes an adjustment pin that is received through an arcuate slot on the alignment member to engage a recess on the tool body, and includes a guide plate extending from an end of the tool body and is triangularly shaped to be received within a guide slot formed in an arcuate guiding protrusion of the alignment member, wherein the guide plate includes a cooperating curved surface to engage the arcuate guiding protrusion.

2. The surgical guiding tool as claimed in claim 1, wherein the adjustment mechanism is configured to direct rotational adjustment of the alignment member in the reference plane of the tool.

3. The surgical guiding tool as claimed in claim 1, further comprising a referencing rod that is connectable to the alignment member and operable for alignment with a reference axis.

4. The surgical guiding tool as claimed in claim 3, wherein the referencing rod is connectable to the alignment member in a predetermined angular relation to the guide surface.

5. The surgical guiding tool as claimed in claim 3, wherein the guide surface is planar and the referencing rod is connectable to the alignment member such that a longitudinal axis of the referencing rod is substantially normal to the plane of the guide surface.

6. The surgical guiding tool as claimed in claim 3, wherein the referencing rod is connectable to the alignment member via a threaded connection.

7. The surgical guiding tool as claimed in claim 3, wherein the referencing rod is operable for alignment with a fibula of a patient.

8. The surgical guiding tool as claimed in claim 1, wherein the arcuate slot is elongated to allow rotation of the alignment member about the adjustment pin along the reference plane.

9. The surgical guiding tool as claimed in claim 1, further comprising an indicator, operable to indicate a default position of rotational adjustment in which the guide surface of the alignment member is in a predetermined angular relation to the reference plane of the tool.

10. The surgical guiding tool as claimed in claim 9, wherein the indicator comprises a protrusion formed on one of the tool body and the alignment member and a corresponding recess formed on the other of the tool body and the alignment member.

11. The surgical guiding tool as claimed in claim 10, wherein the protrusion comprises a spring mounted ball and the recess comprises a groove extending along an axis that defines the position at which the alignment member is in the predetermined angular relation with the reference plane of tool.

12. The surgical guiding tool as claimed in claim 1, wherein the tool body comprises a tool stem and a translation member which is translatable with respect to the tool stem along a translation axis.

13. The surgical guiding tool as claimed in claim 12, further comprising a threaded driving connection between the tool stem and the translation member, the threaded driving connector including a threaded shaft extending from the translation member and a separate threaded nut threadably connected to the threaded shaft.

14. The surgical guiding tool as claimed in claim 12, wherein the adjustment mechanism acts between the translation member and the alignment member.

15. The surgical guiding tool as claimed in claim 1, wherein the tool body comprises at least two telescoping sections.

16. The surgical guiding tool as claimed in claim 1, wherein the tool body further comprises at least two fixation members disposed at opposed ends of the tool stem.

17. The surgical guiding tool as claimed in claim 16, wherein a first fixation member comprises opposed jaws.

18. The surgical guiding tool as claimed in claim 16, wherein a second fixation member comprises at least two opposed fixation blocks, each fixation block comprising a plurality of guide holes extending there through and operable to receive a plurality of fixation elements.

19. The surgical guiding tool as claimed in claim 1, wherein the guiding tool comprises a guiding tool for an ankle.

20. The surgical guiding tool as claimed in claim 19, wherein the guide surface is a distal tibial cutting guide surface.

21. The surgical guiding tool as claimed in claim 1, wherein, in use, the reference plane of the tool is parallel to a coronal plane of a patient.

* * * * *

UNITED STATES PATENT AND TRADEMARK OFFICE
CERTIFICATE OF CORRECTION

PATENT NO. : 9,445,823 B2
APPLICATION NO. : 13/700933
DATED : September 20, 2016
INVENTOR(S) : Harris et al.

Page 1 of 1

It is certified that error appears in the above-identified patent and that said Letters Patent is hereby corrected as shown below:

On the Title Page

In item (73), in "Assignee", in Column 1, Line 1, after "Limited", insert --, Bridgend, South Wales--, therefor Signed and Sealed this
Thirteenth Day of March, 2018

Andrei Iancu
*Director of the United States Patent and Trademark Office*